US010525452B2

(12) United States Patent
Liu et al.

(10) Patent No.: US 10,525,452 B2
(45) Date of Patent: Jan. 7, 2020

(54) NA-Y MOLECULAR SIEVE, H-Y MOLECULAR SIEVE, AND PREPARATION METHODS THEREOF, HYDROCRACKING CATALYST, AND HYDROCRACKING METHOD

(71) Applicants: China Petroleum & Chemical Corporation, Beijing (CN); Fushun Research Institute of Petroleum and Petrochemicals, SINOPEC CORP., Fushun, Liaoning (CN)

(72) Inventors: Chang Liu, Liaoning (CN); Fenglai Wang, Liaoning (CN); Minghua Guan, Liaoning (CN); Yanze Du, Liaoning (CN); Wei Huang, Liaoning (CN); Hong Zhao, Liaoning (CN)

(73) Assignees: CHINA PETROLEUM & CHEMICAL CORPORATION, Beijing (CN); FUSHUN RESEARCH INSTITUTE OF PETROLEUM AND PETROCHEMICALS, INOPEC CORP., Fushun, Liaoning (CN)

( * ) Notice: Subject to any disclaimer, the term of this patent is extended or adjusted under 35 U.S.C. 154(b) by 0 days.

(21) Appl. No.: 16/272,148

(22) Filed: Feb. 11, 2019

(65) Prior Publication Data
US 2019/0168193 A1 Jun. 6, 2019

Related U.S. Application Data

(62) Division of application No. 14/946,527, filed on Nov. 19, 2015, now Pat. No. 10,265,687.

(30) Foreign Application Priority Data

Dec. 1, 2014 (CN) .......................... 2014 1 0711208
Dec. 1, 2014 (CN) .......................... 2014 1 0711228
Dec. 1, 2014 (CN) .......................... 2014 1 0711239

(51) Int. Cl.
| | | |
|---|---|---|
| *B01J 29/08* | (2006.01) | |
| *C01B 39/24* | (2006.01) | |
| *C07C 4/06* | (2006.01) | |
| *C10G 47/20* | (2006.01) | |
| *B01J 29/16* | (2006.01) | |
| *B01J 35/10* | (2006.01) | |
| *B01J 29/10* | (2006.01) | |
| *B01J 35/02* | (2006.01) | |
| *C01B 39/46* | (2006.01) | |

(52) U.S. Cl.
CPC ........... *B01J 29/166* (2013.01); *B01J 29/084* (2013.01); *B01J 29/106* (2013.01); *B01J 35/023* (2013.01); *B01J 35/1028* (2013.01); *B01J 35/1038* (2013.01); *B01J 35/1061* (2013.01); *C01B 39/24* (2013.01); *C01B 39/46* (2013.01); *C07C 4/06* (2013.01); *C10G 47/20* (2013.01); *B01J 35/108* (2013.01); *B01J 2229/20* (2013.01); *C01P 2004/61* (2013.01); *C01P 2006/14* (2013.01); *C01P 2006/17* (2013.01)

(58) Field of Classification Search
CPC ....... C01B 39/24; B01J 29/084; B01J 29/106; B01J 29/166; B01J 35/023; B01J 35/1028; B01J 35/1038; B01J 35/1061; B01J 35/108; B01J 2229/20; C01P 2004/61; C01P 2006/14; C01P 2006/17; C07C 4/06; C10G 47/20
See application file for complete search history.

(56) References Cited

U.S. PATENT DOCUMENTS

| | | | |
|---|---|---|---|
| 3,639,099 A | 2/1972 | Elliott, Jr. et al. | |
| 3,671,191 A | 6/1972 | Maher et al. | |
| 4,826,587 A | 5/1989 | Ward et al. | |
| 4,857,169 A | 8/1989 | Abdo | |
| 7,026,262 B1 | 4/2006 | Palmas et al. | |
| 10,265,687 B2 * | 4/2019 | Liu ...................... | B01J 35/1061 |

FOREIGN PATENT DOCUMENTS

| | | |
|---|---|---|
| CN | 1056473 A | 11/1991 |
| CN | 1179400 A | 4/1998 |
| CN | 1209358 A | 3/1999 |
| CN | 1417117 A | 5/2003 |
| CN | 1621348 A | 6/2005 |
| CN | 1634764 A | 7/2005 |
| CN | 1683246 A | 10/2005 |
| CN | 101254929 A | 9/2008 |
| CN | 101380588 A | 3/2009 |
| CN | 101481120 A | 7/2009 |
| CN | 101618334 A | 1/2010 |
| CN | 101618881 A | 1/2010 |
| CN | 101723400 A | 6/2010 |
| CN | 101947430 A | 1/2011 |
| CN | 102049279 A | 5/2011 |

(Continued)

OTHER PUBLICATIONS

Intellectual Property India, Examination Report for parallel Indian Application No. 1211/KOL/2015, dated May 4, 2018.

*Primary Examiner* — David M Brunsman
(74) *Attorney, Agent, or Firm* — Novick, Kim & Lee, PLLC; Allen Xue

(57) ABSTRACT

Provided is a Na—Y molecular sieve and a method for preparing the Na—Y molecular sieve, an H—Y molecular sieve and a method for preparing the H—Y molecular sieve, a hydrocracking catalyst, and a hydrocracking method. The average grain diameter of the Na—Y molecular sieve is 2-5 μm, and the sum of pore volumes of pores in 1-10 nm diameter accounts for 70-90% of the total pore volume of the Na—Y molecular sieve. The H—Y molecular sieve obtained from the large-grain Na—Y molecular sieve can be used as an acidic component in the hydrocracking catalyst. When the hydrocracking catalyst containing the H—Y molecular sieve is applied in the hydrocracking reaction of heavy oils that contain macromolecules, it can provide better cracking activity and product selectivity in the hydrocracking reaction.

7 Claims, 2 Drawing Sheets

(56) References Cited

FOREIGN PATENT DOCUMENTS

| | | |
|---|---|---|
| CN | 101380589 B | 7/2011 |
| CN | 102442685 A | 5/2012 |
| CN | 103449468 A | 12/2013 |
| CN | 102806098 B | 5/2014 |
| CN | 104588122 A | 5/2015 |
| CN | 104591207 A | 5/2015 |
| CN | 104591214 A | 5/2015 |
| CN | 104773741 A | 7/2015 |
| CN | 104828839 A | 8/2015 |
| CN | 104591212 B | 6/2016 |
| CN | 105709845 A | 6/2016 |
| GB | 2535584 A | 8/2016 |
| JP | 08-057328 A | 3/1996 |
| JP | 2003137538 A | 5/2003 |

\* cited by examiner

NA-Y MOLECULAR SIEVE, H-Y MOLECULAR SIEVE, AND PREPARATION METHODS THEREOF, HYDROCRACKING CATALYST, AND HYDROCRACKING METHOD

CROSS REFERENCE TO RELATED APPLICATION

This application is a divisional application of U.S. application Ser. No. 14/946,527 filed on Nov. 19, 2015, now U.S. Pat. No. 10,265,687, which claims priority to Chinese Application No. 201410711228.1 filed on Dec. 1, 2014, entitled "A NaY Molecular Sieve and Method for Preparing the same", Chinese Application No. 201410711208.4 filed on Dec. 1, 2014, entitled "A Y Molecular Sieve and Method for Preparing the same", and Chinese Application No. 201410711239.x filed on Dec. 1, 2014, entitled "Modified Y Molecular Sieve and Method for Preparing the same", which are hereby specifically and entirely incorporated by reference.

FIELD OF THE INVENTION

The present invention relates to a Na—Y molecular sieve and a method for preparing the Na—Y molecular sieve, an H—Y molecular sieve obtained from the molecular sieve and a method for preparing the H—Y molecular sieve, a hydrocracking catalyst containing the H—Y molecular sieve, and a hydrocracking method utilizing the hydrocracking catalyst.

BACKGROUND OF THE INVENTION

At present, in the heavy oil cracking field, molecular sieves that can be used as cracking active components include Y molecular sieve, β molecular sieve, and ZSM molecular sieve, etc., wherein Y molecular sieve is used most widely. Existing methods for producing Y molecular sieve products in industrial production are essentially based on the method of using a crystallization directing agent (CDA) disclosed by GRACE Company (a US company) in the U.S. Pat. Nos. 3,639,099 and 4,166,099, and the ordinary Y molecular sieve products produced with such methods have crystal grains usually in about 1 μm grain size, with about 300-400 crystal cells in each dimension. In Y molecular sieve powder in ordinary grain size synthesized conventionally, the distribution percentage of pores in diameter smaller than 1 nm is 15-20%, the distribution percentage of pores in diameter within 1-10 nm range is 45-50%, and the distribution percentage of pores in diameter greater than 10 nm is 30-40%. For a macromolecular cracking reaction, the ideal pore diameter range suitable for raw material reaction and product diffusion is 1-10 nm. Though Y molecular sieve can be modified appropriately to an ideal pore diameter distribution range by post-modification, the final distribution of pore diameter range in the post-modified molecular sieve directly depends on the original pore diameter distribution in the molecular sieve; moreover, pore expansion has impacts on the skeleton structure of the molecular sieve, and thereby has impacts on the activity and stability of the molecular sieve.

In the prior art, the direct synthesis process refers to a process in which a Y molecular sieve (usually Na—Y molecular sieve) to be prepared is synthesized directly in one operation without post-treatment. At present, a CDA method is used conventionally. With that method, the chemical silica-alumina ratio ($SiO_2/Al_2O_3$) in the synthesized Y molecular sieve is 3.5-5.5. To obtain a Y molecular sieve with a higher chemical silica-alumina ratio, expensive and highly toxic organic materials such as crown ether have to be added. In addition, in the preparation process of a Y molecular sieve, the lower the silica-alumina ratio is, the easier the preparation is; in contrast, the higher the silica-alumina ratio is, the harsher the conditions are, and the more difficult the preparation is. There are many influencing factors in preparation of a molecular sieve with a high silica-alumina ratio, such as the composition of the reaction mixture, the preparation method, the source of the reactants, the preparation of the directing agent, the acidity/alkalinity of the gel, and the conditions of crystallization, etc.

In CN103449468A, a Na—Y molecular sieve synthesis method is disclosed, comprising: mixing sodium silicate, sodium metaaluminate, and deionized water, and aging at 15-70° C. for 0.5-48.0 h to obtain a crystallization directing agent; mixing the crystallization directing agent, sodium silicate, an acidic aluminum salt, and sodium aluminate solution to a homogeneous state to prepare a silica-alumina gel; crystallizing the silica-alumina gel at 80-140° C. for 0.1-80.0h; adding peroxide into the crystallized silica-alumina gel at a mole ratio of peroxide to $Al_2O_3$ in the gel equal to 0.05-20, and then continuing the crystallization for 5-20h. With that method, no organic or inorganic template agent is added, no post-treatment or modification is required, and a Y molecular sieve with a high silica-alumina ratio can be prepared directly in a short time, and crystallinity of the obtained molecular sieve is equal to or higher than 80%, silica-alumina ratio not lower than 5.8, and average grain diameter within 200-300 nm range. Though that method can be used to synthesize a Y molecular sieve with high silica-alumina ratio, the preparation process is complex, the grain diameter of the obtained molecular sieve is too small, and a specific amount of peroxide has to be added into the gel. Hence, the conditions of molecular sieve synthesis are demanding.

In U.S. Pat. Nos. 3,671,191 and 3,639,099, a CDA method is used to synthesize a Y molecular sieve, wherein a directing agent is prepared first; then, a silica-alumina gel is prepared; next, the aged directing agent is added, and crystallization is carried out at a high temperature. In the method described above, an inorganic acid and an aluminum salt are used to decrease the alkalinity of the reaction system, and thereby improve the silica-alumina ratio of the resultant molecular sieve. However, only an ordinary Y molecular sieve can be prepared with that method, and a directing agent has to be synthesized first in the preparation process. In addition, the preparation process involves over many steps and high cost.

In CN101481120A, a method for preparation of a Y molecular sieve through a rapid crystallization process is disclosed. In that method, first, a silica-alumina gel is prepared from a silica source, an alumina source, and an alkali source; then, a W/O emulsion system is prepared from the silica-alumina gel, oil, surfactant, and co-surfactant; next, the W/O emulsion system is transferred into a reactor for rapid crystallization. The method employs an expansive surfactant to prepare the Y molecular sieve, and the preparation process is complex; consequently, the preparation cost is severely increased.

In CN1209358A, a Y zeolite rich in secondary pores is disclosed. Specifically, a method for preparation of a zeolite is disclosed, wherein Na—Y zeolite is used as the initial powder, and ammonium exchange is carried out first, to release Na+; then, hydrothermal treatment and acid extraction are carried out twice, wherein the second round of hydrothermal treatment and second round of acid extraction are carried out after the first round of hydrothermal treatment and first round of acid extraction. In the obtained Y zeolite, the pore volume of pores in diameter greater than 2 nm accounts for 40-66% of the total pore volume. In hydrocracking process, the transformation of macromolecular aromatics in the raw material is affected adversely, and the distribution and quality of the prepared catalyst product should be further improved.

Viewed from the aspect of application of molecular sieve products with a cracking function in industrial catalytic processes, the performance of molecular sieve products mainly depend on the two aspects: selective absorptivity and reactivity. The molecules of the reactants can diffuse into the pore canals of the molecular sieve and have specific catalyzed reactions only if the molecular size of the reactant is smaller than the pore size of the molecular sieve and the molecules can overcome the surface energy barrier of the crystals in the molecular sieve; here, the diffusivity of the absorbed molecules through the pores and cages of the crystals in the molecular sieve plays a decisive role. Hence, it is desirable to overcome the drawback of existing Y molecular sieve products in ideal pore diameter distribution and provide a Y molecular sieve with pore diameter distribution suitable for macromolecular cracking reactions.

SUMMARY OF THE INVENTION

To overcome the drawbacks in the prior art, the present invention provides a Na—Y molecular sieve, a H—Y molecular sieve and a method for preparing the Na—Y molecular sieve, a H—Y molecular sieve and a method for preparing the H—Y molecular sieve, a hydrocracking catalyst, and a hydrocracking method.

To attain the objects described above, the present invention provides a Na—Y molecular sieve, wherein the average grain diameter of the Na—Y molecular sieve is 2-5 µm, and the sum of pore volumes of pores in 1-10 nm diameter accounts for 70-90% of the total pore volume of the Na—Y molecular sieve.

The present invention further provides a method for preparing the Na—Y molecular sieve provided in the present invention, comprising: (1) mixing sodium silicate, high alkaline sodium metaaluminate solution, aluminum sulfate solution, and low alkaline sodium metaaluminate solution at a mole ratio of $Na_2O:Al_2O_3:SiO_2:H_2O$ equal to (10-15):1:(10-20):(500-600), and aging the obtained mixture to obtain a gel; and (2) treating the gel obtained in step (1) by hydrothermal crystallization, and then filtering, washing, and drying the gel after hydrothermal crystallization.

The present invention further provides an H—Y molecular sieve, wherein the crystal cell parameter of the H—Y molecular sieve is 2.425-2.450 nm; the mole ratio of $SiO_2/Al_2O_3$ in the H—Y molecular sieve is 10-120:1; the sum of pore volumes of pores in 2-7 nm diameter in the H—Y molecular sieve is 60-95% of the total pore volume, preferably is 70-90%; the specific surface area of the H—Y molecular sieve is 750-980 m2/g; and, the total acid amount measured by near infrared spectroscopy in the H—Y molecular sieve is 0.1-1.0 mmol/g.

The present invention further provides a method for preparing a H—Y molecular sieve, comprising: (A) treating the Na—Y molecular sieve provided in the present invention by ammonium exchange to prepare a $NH_4$—Na—Y molecular sieve; (B) treating the $NH_4$—Na—Y molecular sieve obtained in step (A) by hydrothermal treatment; and (C) controlling the material obtained in step (B) to have a contact reaction with $(NH_4)_2SiF_6$ solution.

The present invention further provides an H—Y molecular sieve prepared with the method provided in the present invention.

The present invention further provides a hydrocracking catalyst, wherein the support in the catalyst contains the H—Y molecular sieve provided in the present invention.

The present invention further provides a hydrocracking method, comprising: (a) hydro-pretreating a raw oil, with hydrogen and a pretreating agent in presence; and (b) hydrocracking the pretreated product obtained in step (a), with hydrogen and a hydrocracking catalyst in presence; wherein the hydrocracking catalyst is the hydrocracking catalyst provided in the present invention.

The large-grain Na—Y molecular sieve provided in the present invention has 2-5 µm crystal granularity, high silica-alumina ratio, more concentrated effective pore diameter distribution, high thermostability, and high hydrothermal stability. In the method for preparing the molecular sieve, no additive such as directing agent, template agent or surfactant is added; the product is synthesized by hydrothermal crystallization in one operation, by selecting appropriate raw materials and optimizing the preparation process; in addition, the utilization efficiency of silica source and alumina source is high, the process is brief, and the cost is low.

Moreover, the H—Y molecular sieve obtained from the large-grain Na—Y molecular sieve can be used as an acidic component in the hydrocracking catalyst. Since the large-grain molecular sieve synthesized in the present invention has large crystal grains, with 1,000-2,000 crystal cells in each dimension, it is ideal for using in macromolecular cracking. In addition, the molecular sieve has a better pore diameter distribution range, so that the cracking degree of the reactants can be effectively controlled and it is helpful for diffusion of the product through the pores and channels. Therefore, when a catalyst containing the molecular sieve is applied in a hydrocracking reaction of a heavy oil that contains macromolecules, the molecular sieve can provide more active sites so that the macromolecules in the heavy oil are cracked to an appropriate degree; hence, the catalyst containing the molecular sieve can improve heavy oil cracking capability, decrease coke yield, and provide better cracking activity and product selectivity in the hydrocracking reaction.

Other aspects and advantages of the present invention will be further detailed in the embodiments hereunder.

BRIEF DESCRIPTION OF THE DRAWINGS

The accompanying drawings are provided here to facilitate further understanding on the present invention, and constitute a part of this document. They are used in conjunction with the following embodiments to explain the present invention, but shall not be comprehended as constituting any limitation to the present invention. Among the figures.

DETAILED DESCRIPTION

Figure 1:
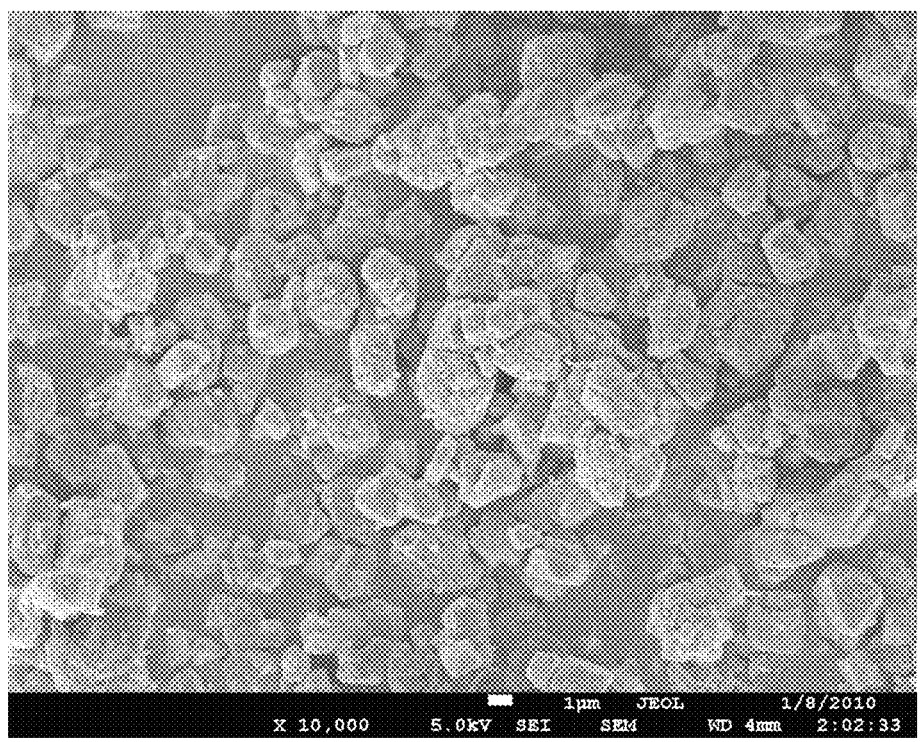
FIG. 1 is a SEM photo of LY-1 obtained in example 1.

Hereunder some embodiments of the present invention will be detailed. It should be appreciated that the embodiments described here are only provided to describe and explain the present invention, but shall not be deemed as constituting any limitation to the present invention.

The present invention provides a Na—Y molecular sieve, wherein the average grain diameter of the Na—Y molecular sieve is 2-5 μm, and the sum of pore volumes of pores in 1-10 nm diameter accounts for 70-90% of the total pore volume of the Na—Y molecular sieve.

The present invention provides a large-grain Na—Y molecular sieve, which, compared with conventional molecular sieves, has larger internal surface area, is more suitable for use as pore and channel structures in macromolecular reactions, provides a chance for secondary cracking and transformation of more macromolecules in the molecular sieve, is more suitable for use in treatment of oil products that contain big molecules or raw materials that contain heavy fractions, and has superior performance in improvement of the transformation probability of macromolecules, etc.

In the present invention, preferably, the average grain diameter is 2-4.5 μm, more preferably is 3-4.5 μm.

In the present invention, preferably, the sum of pore volumes of pores in 1-10 nm diameter accounts for 70-85% of the total pore volume in the Na—Y molecular sieve. In contrast, in Na—Y molecular sieves in the prior art, especially in large-grain Na—Y molecular sieves, the sum of pore volumes of pores in 1-10 nm diameter usually accounts for a percentage lower than 50% of the total pore volume in the Na—Y molecular sieves.

In addition, the large-grain Na—Y molecular sieve provided in the present invention has high silicon content, more concentrated effective pore diameter distribution, and better thermostability and hydrothermal stability.

According to the present invention, the mole ratio of $SiO_2/Al_2O_3$ in the Na—Y molecular sieve is 3.5-6.5:1, preferably is 4-6:1.

According to the present invention, the specific surface area of the Na—Y molecular sieve is 800-1,000 $m^2/g$, the total pore volume of the Na—Y molecular sieve is 0.3-0.4 mL/g, and the external specific surface area of the Na—Y molecular sieve is 60-100 $m^2/g$.

According to the present invention, the relative crystallinity of the Na—Y molecular sieve is 110-150%, and the crystal cell parameter of the Na—Y molecular sieve is 2.46-2.465 nm.

The present invention further provides a method for preparing the Na—Y molecular sieve, comprising: (1) mixing sodium silicate, high alkaline sodium metaaluminate solution, aluminum sulfate solution, and low alkaline sodium metaaluminate solution at a mole ratio of $Na_2O$:$Al_2O_3$:$SiO_2$:$H_2O$ equal to (10-15):1:(10-20):(500-600), and aging the obtained mixture to obtain a gel; and (2) treating the gel obtained in step (1) by hydrothermal crystallization, and then filtering, washing, and drying the gel after hydrothermal crystallization.

In the method for preparing the Na—Y molecular sieve provided in the present invention, no additive such as directing agent, template agent, or surfactant is added in the step (1); the gel to be used to synthesize the molecular sieve is directly prepared from silica source and alumina source materials selected appropriately, and then the large-grain Na—Y molecular sieve is synthesized by hydrothermal crystallization in one operation in the step (2). The Na—Y molecular sieve prepared with that method has 2.0-5.0 μm crystal granularity, high silica-alumina ratio, and more concentrated effective pore diameter distribution; specifically, the distribution percentage of pores in 1 nm-10 nm pore diameter, which are helpful for transformation of macromolecules, is as high as 70%-90%, much higher than that in conventional Y molecular sieves synthesized with the aid of a directing agent.

In the prior art, in the process of preparing a Y molecular sieve with the aid of a directing agent, a directing agent has to be prepared first, and the directing agent has to be aged for days. In the crystallization procedure, the directing agent provides crystal nuclei in the Y molecular sieve, and then the silica source and alumina source in the gel are deposited and crystallized on the crystal nuclei, so that a conventional Y molecular sieve is obtained. In such a conventional Y molecular sieve, the grain diameter is about 1 μm, and the distribution percentage of pores in 1 nm-10 nm diameter is 45%-50%.

In the present invention, in step (1), the sodium silicate, high alkaline sodium metaaluminate solution, aluminum sulfate solution, and low alkaline sodium metaaluminate solution are mixed in the following way: mixing the sodium silicate with the high alkaline sodium metaaluminate solution while stirring, and then mixing the obtained mixture with the aluminum sulfate solution and low alkaline sodium metaaluminate solution. Wherein, water can be added separately or added together with the water solution of alumina source and/or silica source, the silica source is sodium silicate, and the alumina source is aluminum sulfate, high alkaline sodium metalluminate, and low alkaline sodium metaaluminate.

According to the present invention, the aluminum sulfate, high alkaline sodium metaaluminate, and low alkaline sodium metaaluminate control the amount of alumina provided; preferably, in step (1), calculated in $Al_2O_3$, the weight ratio of dosage of aluminum sulfate:high alkaline sodium metaaluminate:low alkaline sodium metaaluminate is 1:(0.5-0.7):(0.6-0.8).

According to the present invention, preferably, in the high alkaline sodium metaaluminate solution, the content of $Na_2O$ is 260-320 g/L, and the content of $Al_2O_3$ is 30-50 g/L.

According to the present invention, in the low alkaline sodium metaaluminate solution, the content of $Na_2O$ is 100-130 g/L, and the content of $Al_2O_3$ is 60-90 g/L.

According to the present invention, in the aluminum sulfate solution, the content of $Al_2O_3$ is 80-100 g/L.

According to the present invention, in the sodium silicate, the content of $SiO_2$ is 200-300 g/L, and the modulus of the sodium silicate is 2.8-3.5.

According to the present invention, preferably, in step (1), the mixing temperature is 20-40° C., preferably is 25-35° C.

According to the present invention, in step (2), the gel is heated to the temperature for hydrothermal crystallization at 2-4° C./min., and then is treated by hydrothermal crystallization.

According to the present invention, in step (2), the hydrothermal crystallization is carried out at 80-120° C. temperature for 12-24h.

The present invention further provides an H—Y molecular sieve, wherein the crystal cell parameter of the H—Y molecular sieve is 2.425-2.450 nm; the mole ratio of $SiO_2/Al_2O_3$ in the H—Y molecular sieve is 10-120:1; the sum of pore volumes of pores in 2-7 nm diameter in the H—Y molecular sieve is 60-95% of the total pore volume, preferably is 70-90%; the specific surface area of the H—Y molecular sieve is 750-980 $m^2/g$; and, the total acid amount measured by near infrared spectroscopy in the H—Y molecular sieve is 0.1-1.0 mmol/g.

According to the present invention, in a preferred embodiment of the present invention, specifically, the average grain diameter of the H—Y molecular sieve is 2-5 μm, preferably is 2-4.5 μm, more preferably is 3-4.5 μm.

The relative crystallinity of the H—Y molecular sieve is 110-150%.

The crystal cell parameter of the H—Y molecular sieve is 2.436-2.450 nm.

The mole ratio of $SiO_2/Al_2O_3$ in the H—Y molecular sieve is 10-50:1.

In the H—Y molecular sieve, the sum of pore volumes of pores in 2-6 nm diameter accounts for 60-90% of the total pore volume, preferably accounts for 70-85%.

The total pore volume of the H—Y molecular sieve is 0.35-0.50 $cm^3/g$.

The specific surface area of the H—Y molecular sieve is 750-950 $m^2/g$.

In the H—Y molecular sieve, the amount of non-skeleton aluminum accounts for 0.1-1% of the total amount of aluminum, preferably accounts for 0.1-0.5%.

The total acid amount measured by near infrared spectroscopy (NIS) in the H—Y molecular sieve is 0.5-1.0 mmol/g.

The content of $Na_2O$ in the H—Y molecular sieve is 0.15 wt % or lower.

According to the present invention, in another preferred embodiment of the present invention, specifically, the average grain diameter of the H—Y molecular sieve is 2-5 μm, preferably is 2-4.5 μm, more preferably is 3-4.5 μm.

The relative crystallinity of the H—Y molecular sieve is 110-150%.

The crystal cell parameter of the H—Y molecular sieve is 2.425-2.435 nm, preferably is 2.427-2.434 nm.

The mole ratio of $SiO_2/Al_2O_3$ in the H—Y molecular sieve is 60-120:1.

In the H—Y molecular sieve, the sum of pore volumes of pores in 3-7 nm diameter in the H—Y molecular sieve is 70-95% of the total pore volume, preferably is 75-90%.

The total pore volume of the H—Y molecular sieve is 0.35-0.50 $cm^3/g$.

The specific surface area of the H—Y molecular sieve is 800-980 $m^2/g$.

In the H—Y molecular sieve, the amount of non-skeleton aluminum accounts for 0.1-1.0% of the total amount of aluminum, preferably accounts for 0.1-0.5%.

The total acid amount measured by NIS in the H—Y molecular sieve is 0.1-0.5 mmol/g.

The present invention further provides a method for preparing a H—Y molecular sieve, comprising: (A) treating the Na—Y molecular sieve provided in the present invention by ammonium exchange to prepare a $NH_4$—Na—Y molecular sieve; (B) treating the $NH_4$—Na—Y molecular sieve obtained in step (A) by hydrothermal treatment, under the following conditions: 0.05-0.25 MPa gage pressure, 400-550° C. temperature, and 0.5-5 h treatment time; and (C) controlling the material obtained in step (B) to have a contact reaction with $(NH_4)_2SiF_6$ solution.

According to the present invention, the ammonium exchange can be repeated for several times, as long as the content of $Na_2O$ in the $NH_4$—Na—Y molecular sieve after the ammonium exchange is acceptable. Preferably, the content of $Na_2O$ in the $NH_4$—Na—Y molecular sieve obtained in step (A) is 2.5-5 wt %.

In the present invention, the ammonium salt can be one or more of ammonium chloride, ammonium nitrate, ammonium sulfate, ammonium acetate, and ammonium oxalate, and the concentration of the water solution of ammonium salt can be 0.3-6 mol/L.

In a preferred embodiment of the present invention, in step (B), the conditions of hydrothermal treatment include: gage pressure: 0.05-0.25 MPa, preferably 0.1-0.2 MPa; temperature: 400-550° C., preferably 450-550° C.; time: 0.5-5 h, preferably 1-3h.

In step (C), the material obtained in step (B) is mixed with $(NH_4)_2SiF_6$ solution at weight ratio of liquid:solid equal to 3:1-8:1 at 70-90° C., and then the obtained mixture is held at 80-120° C. for 0.5-5h for reaction, wherein in relation to 100 pbw $NH_4$—Na—Y molecular sieve, the dosage of the $(NH_4)_2SiF_6$ is 10-35 pbw; more preferably, in each hour, in relation to 100 pbw $NH_4$—Na—Y molecular sieve, the dosage of the $(NH_4)_2SiF_6$ is 3-30 pbw.

According to the preferred embodiment, the present invention further provides an H—Y molecular sieve prepared with the method provided in the present invention.

Specifically, the average grain diameter of the H—Y molecular sieve is 2-5 μm, preferably is 2-4.5 μm, more preferably is 3-4.5 μm.

The relative crystallinity of the H—Y molecular sieve is 110-150%, and the crystal cell parameter of the H—Y molecular sieve is 2.436-2.450 nm.

The mole ratio of $SiO_2/Al_2O_3$ in the H—Y molecular sieve is 10-50:1.

In the H—Y molecular sieve, the sum of pore volumes of pores in 2-6 nm diameter accounts for 60-90% of the total pore volume, preferably accounts for 70-85%.

The total pore volume of the H—Y molecular sieve is 0.35-0.50 $cm^3/g$, and the specific surface area of the H—Y molecular sieve is 750-950 $m^2/g$.

In the H—Y molecular sieve, the amount of non-skeleton aluminum accounts for 0.1-1% of the total amount of aluminum, preferably accounts for 0.1-0.5%.

The total acid amount measured by NIS in the H—Y molecular sieve is 0.5-1.0 mmol/g.

The content of $Na_2O$ in the H—Y molecular sieve is 0.15 wt % or lower.

In another preferred embodiment of the present invention, in step (B), the conditions of hydrothermal treatment include: gage pressure: 0.28-0.5 MPa, preferably 0.3-0.5 MPa; temperature: 450-700° C., preferably 600-700° C.; time: 0.5-5h, preferably 1-3h.

In step (C), the material obtained in step (B) is mixed with $(NH_4)_2SiF_6$ solution at weight ratio of liquid:solid equal to 8:1-15:1 at 95-130° C., and then the obtained mixture is held at 80-120° C. for 0.5-5h for reaction, wherein in relation to 100 pbw $NH_4$—Na—Y molecular sieve, the dosage of the $(NH_4)_2SiF_6$ is 35-80 pbw; more preferably, in each hour, in relation to 100 pbw $NH_4$—Na—Y molecular sieve, the dosage of the $(NH_4)_2SiF_6$ is 3-30 pbw.

According to the above preferred embodiment, the present invention further provides an H—Y molecular sieve prepared with the method provided in the present invention.

Specifically, the average grain diameter of the H—Y molecular sieve is 2-5 μm, preferably is 2-4.5 μm, more preferably is 3-4.5 μm.

The relative crystallinity of the H—Y molecular sieve is 110-150%, and the crystal cell parameter of the H—Y molecular sieve is 2.425-2.435 nm, preferably is 2.427-2.434 nm.

The mole ratio of $SiO_2/Al_2O_3$ in the H—Y molecular sieve is 60-120:1.

In the H—Y molecular sieve, the sum of pore volumes of pores in 3-7 nm diameter accounts for 70-95% of the total pore volume, preferably accounts for 75-90%.

The total pore volume of the H—Y molecular sieve is 0.35-0.50 cm³/g, and the specific surface area of the H—Y molecular sieve is 800-980 m²/g.

In the H—Y molecular sieve, the amount of non-skeleton aluminum accounts for 0.1-1.0% of the total amount of aluminum, preferably accounts for 0.1-0.5%.

The total acid amount measured by NIS in the H—Y molecular sieve is 0.1-0.5 mmol/g.

The content of $Na_2O$ in the H—Y molecular sieve is 0.15 wt % or lower.

The present invention further provides a hydrocracking catalyst, wherein the support in the catalyst contains the H—Y molecular sieve provided in the present invention.

According to the present invention, preferably, the content of the H—Y molecular sieve in the support is 15-90 wt %. The support can further contain amorphous silica-alumina and/or alumina. According to the present invention, preferably, the specific surface area of the catalyst is 200-400 m²/g, and the pore volume of the catalyst is 0.2-0.5 ml/g.

The catalyst can further comprise hydrogenation active components.

According to the present invention, preferably, the hydrogenation active components are a metal element in VIB Family and a metal element in VIII Family; preferably, the metal element in VIB Family is Mo and/or W, and the metal element in VIII Family is Co and/or Ni.

According to the present invention, preferably, based on the total weight of the catalyst and calculated in metal oxide, the content of the metal element in VIB Family is 10-40 wt %, and the content of the metal element in VIII Family is 3-15 wt %; the content of the support is 45-87 wt %.

The present invention further provides a hydrocracking method, comprising: (a) hydro-pretreating a raw oil in presence of hydrogen and a pretreating agent; and (b) hydrocracking the pretreated product obtained in step (a), in presence of hydrogen and a hydrocracking catalyst, wherein the hydrocracking catalyst is the hydrocracking catalyst provided in the present invention.

According to the present invention, preferably, the conditions of hydro-pretreatment in step (a) include: 6-20 MPa reaction pressure, 350-420° C. reaction temperature, 0.1-2h⁻¹ volumetric space velocity of input of the raw oil, and 500:1-2,000:1 volume ratio of hydrogen to the raw oil.

According to the present invention, preferably, the conditions of hydrocracking in step (b) include: 6-20 MPa reaction pressure, 350-420° C. reaction temperature, 0.1-2h⁻¹ volumetric space velocity of input of the pretreatment product, and 500:1-2,000:1 volume ratio of hydrogen gas to the pretreatment product.

Hereunder the present invention will be further detailed in some embodiments.

In the following examples and comparative examples, the specific surface area, pore volume, external specific surface area, and pore distribution are measured with an ASAP2420 cryogenic nitrogen adsorption analyzer from Micromeritics, with the cryogenic nitrogen physical adsorption method defined in GB/T 19587-2004;

The relative crystallinity and crystal cell parameter are measured with a Dmax-2500 X-ray diffractometer from Rigaku, with an X-ray diffraction method;

The silica-alumina mole ratio is measured with a ZSX100e XRF analyzer from Rigaku, with chemical analysis method.

The grain size of the molecular sieve is measured with a JEM-7500L SEM from JEOL.

Example 1

(1) Preparation of gel: add 165 mL sodium silicate (the $SiO_2$ content is 235 g/L, the modulus is 2.9) into 63 mL high alkaline sodium metaaluminate solution (the $Na_2O$ content is 280 g/L, the $Al_2O_3$ content is 35 g/L) slowly at 25° C. while stirring; after the mixture is mixed to a homogeneous state, add 42.5 mL aluminum sulfate solution (the $Al_2O_3$ content is 85 g/L) and 35.6 mL low alkaline sodium metaaluminate solution (the $Na_2O$ content is 110 g/L, and the $Al_2O_3$ content is 68 g/L) sequentially, and stir for 0.5h at the temperature; then, hold the obtained synthetic liquid at the temperature for 1h for aging; thus, a gel is obtained;

(2) Crystallization: heat up the gel in the synthesis reactor at 2.5° C./min heating rate to 100° C. while stirring, and then stir for 16h at the temperature for crystallization; next, cool down with cold water quickly, and take out the synthesized molecular sieve from the synthesis reactor, filter, wash, and dry the molecular sieve; thus, a large-grain Na—Y molecular sieve product LY-1 is obtained. The properties of the product are shown in Table 1.

Observe LY-1 on a SEM and carry out XRD analysis. The SEM photo is shown in FIG. 1. It can be seen that the grain size of the molecular sieve obtained in the present invention is 3.5 μm, which is very large, and the crystal grains are uniform.

Figure 3:
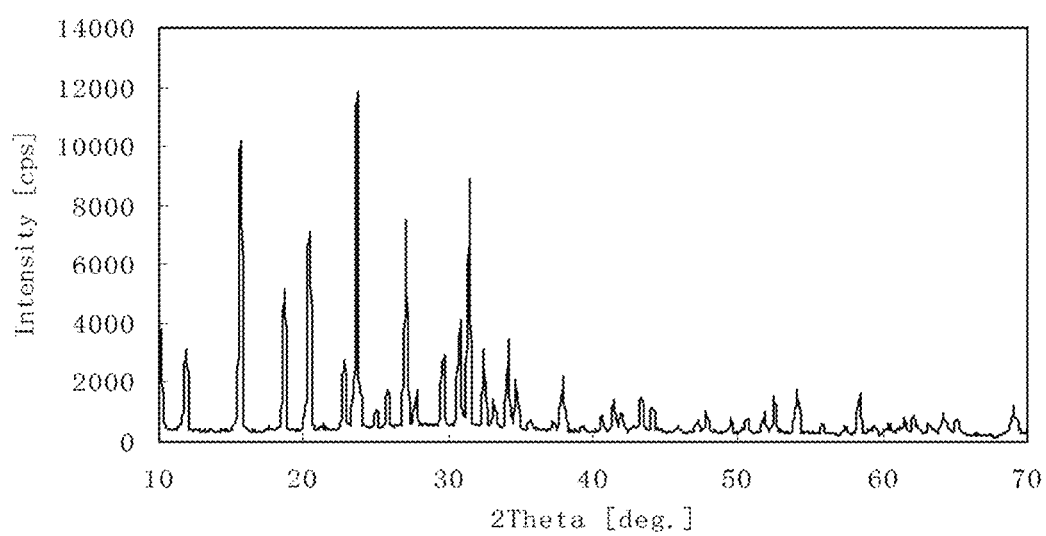
FIG. 3 is a XRD diagram of LY-1 obtained in example 1.

The XRD diagram is shown in FIG. 3. It can be seen that the large-grain Y molecular sieve obtained in the present invention has obvious characteristic peaks, indicating that the molecular sieve prepared with the method disclosed in the present invention has integral crystal morphology and relative high crystallinity.

Example 2

(1) Preparation of gel: add 170 mL sodium silicate (the $SiO_2$ content is 235 g/L, the modulus is 2.9) into 56 mL high alkaline sodium metaaluminate solution (the $Na_2O$ content is 275 g/L, the $Al_2O_3$ content is 40 g/L) slowly at 30° C. while stirring; after the mixture is mixed to a homogeneous state, add 45.6 mL aluminum sulfate solution (the $Al_2O_3$ content is 90 g/L) and 39.8 mL low alkaline sodium metaaluminate solution (the $Na_2O$ content is 120 g/L, and the $Al_2O_3$ content is 77 g/L) sequentially, and stir for 0.5h at a constant stirring rate at the temperature; then, hold the obtained synthetic liquid at the temperature for 1h for aging; thus, a gel is obtained;

(2) Crystallization: heat up the gel in the synthesis reactor at 3° C./min. heating rate to 120° C. while stirring, and then stir for 20h at the temperature for crystallization; next, cool down with cold water quickly, and take out the synthesized molecular sieve from the synthesis reactor, filter, wash, and dry the molecular sieve; thus, a large-grain Na—Y molecular sieve product LY-2 is obtained. The properties of the product are shown in Table 1.

Observe LY-2 on a SEM and carry out XRD analysis. The results obtained are similar to those shown in FIG. 1 and FIG. 3, and are not shown here.

Example 3

(1) Preparation of gel: add 156 mL sodium silicate (the $SiO_2$ content is 260 g/L, the modulus is 3.0) into 48 mL high alkaline sodium metaaluminate solution (the $Na_2O$ content is 300 g/L, the $Al_2O_3$ content is 45 g/L) slowly at 35° C. while stirring; after the mixture is mixed to a homogeneous state, add 39.6 mL aluminum sulfate solution (the $Al_2O_3$ content is 90 g/L) and 28.5 mL low alkaline sodium metaaluminate solution (the $Na_2O$ content is 120 g/L, and the $Al_2O_3$ content is 82 g/L) sequentially, and stir for 1 h at a constant stirring rate at the temperature; then, hold the obtained synthetic liquid at the temperature for 2h for aging; thus, a gel is obtained;

(2) Crystallization: heat up the gel in the synthesis reactor at 3° C./min. heating rate to 110° C. while stirring, and then stir for 24h at the temperature for crystallization; next, cool down with cold water quickly, and take out the synthesized molecular sieve from the synthesis reactor, filter, wash, and dry the molecular sieve; thus, a large-grain Na—Y molecular sieve product LY-3 is obtained. The properties of the product are shown in Table 1.

Observe LY-3 on a SEM and carry out XRD analysis. The results obtained are similar to those shown in FIG. 1 and FIG. 3, and are not shown here.

Example 4

(1) Preparation of gel: add 156 mL sodium silicate (the $SiO_2$ content is 280 g/L, the modulus is 3.0) into 52.5 mL high alkaline sodium metaaluminate solution (the $Na_2O$ content is 280 g/L, the $Al_2O_3$ content is 35 g/L) slowly at 35° C. while stirring; after the mixture is mixed to a homogeneous state, add 47.9 mL aluminum sulfate solution (the $Al_2O_3$ content is 85 g/L) and 42.3 mL low alkaline sodium metaaluminate solution (the $Na_2O$ content is 120 g/L, and the $Al_2O_3$ content is 70 g/L) sequentially, and stir for 1 h at a constant stirring rate at the temperature; then, hold the obtained synthetic liquid at the temperature for 2h for aging; thus, a gel is obtained;

(2) Crystallization: heat up the gel in the synthesis reactor at 3° C./min. heating rate to 120° C. while stirring, and then stir for 24h at the temperature for crystallization; next, cool down with cold water quickly, and take out the synthesized molecular sieve from the synthesis reactor, filter, wash, and dry the molecular sieve; thus, a large-grain Na—Y molecular sieve product LY-4 is obtained. The properties of the product are shown in Table 1.

Observe LY-4 on a SEM and carry out XRD analysis. The results obtained are similar to those shown in FIG. 1 and FIG. 3, and are not shown here.

Comparative Example 1

Prepare a molecular sieve with the CDA method disclosed in U.S. Pat. No. 3,639,099. The Preparation process is as follows: preparation of a directing agent: dissolve 26 g aluminum hydroxide in 153 g sodium hydroxide and 279 mL water to form a raw material A; add 525 g sodium silicate (the $SiO_2$ content is 150 g/L, and the modulus is 3.3) into the raw material A, stir the gel quickly and then hold for 24h at room temperature for aging;

Add 601 g aluminum sulfate solution (content of the aluminum sulfate is calculated in $Al_2O_3$, =16.9 wt %) into 2223 g sodium silicate at 37.8° C., and then add 392 g directing agent into the solution and stir to a homogeneous state; next, add 191 g sodium aluminate solution (containing 126 g aluminum hydroxide and 96.5 g sodium hydroxide), stir the solution quickly, and then treat the solution by hydrothermal crystallization for 10h at 98.8° C.; thus, a Na—Y molecular sieve DLY-1 is obtained; the physical and chemical properties of DLY-1 are shown in Table 1.

Figure 2:
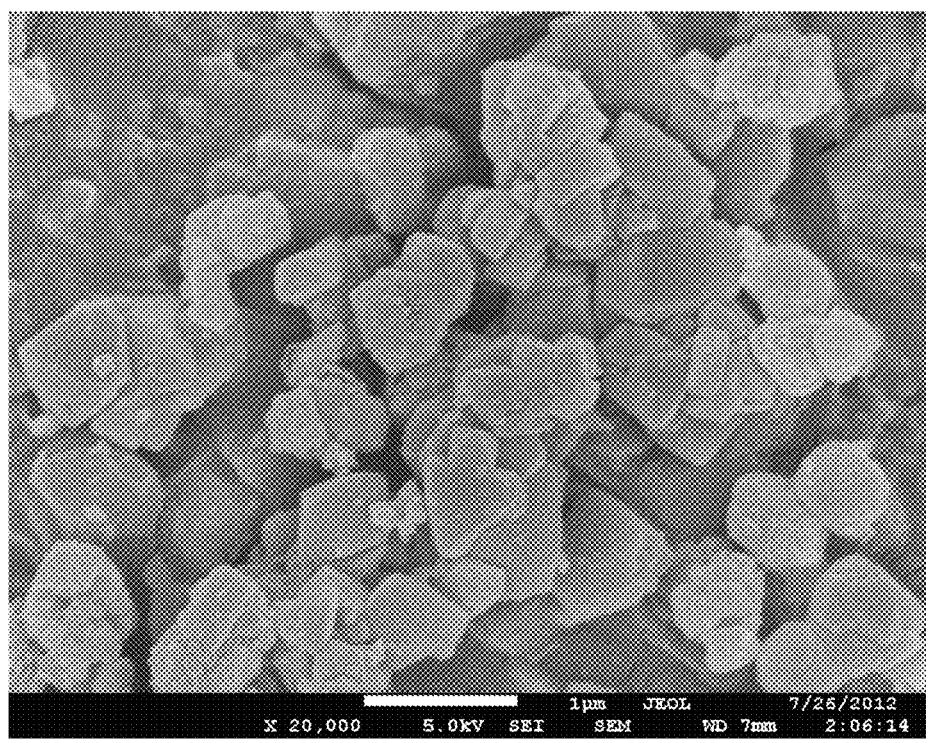
FIG. 2 is a SEM photo of DLY-1 obtained in comparative example 1.

Observe DLY-1 on a SEM and carry out XRD analysis. The SEM photo is shown in FIG. 2. It can be seen that the molecular sieve prepared with the method described in the comparative example 1 has 1.0 μm grain size, which indicates that the Y molecular sieve prepared with the method described in the comparative example 1 is a conventional molecular sieve.

Comparative Example 2

Prepare a molecular sieve with the method disclosed in CN101481120A. Mix and stir 0.699 g silicasol (40 wt %), 0.156 g sodium hydroxide, 0.212 g sodium aluminate, and 2.94 mL deionized water at room temperature to a homogeneous state to obtain white gel; then, add 2.4 g OP10, 1.6 g n-butyl alcohol, and 1.8 mL cyclohexane, stir to a homogeneous state, and treat by hydrothermal crystallization for 24h at 100° C.; thus, a product DLY-2 is obtained; the product properties are shown in Table 1.

Comparative Example 3

Preparation of a directing agent: dissolve 153 g solid sodium hydroxide in 279 mL deionized water, cool down the solution to room temperature, add 22.5 g sodium metaaluminate to prepare high alkaline sodium metaaluminate solution (the $Na_2O$ content is 140 g/L, and the $Al_2O_3$ content is 25 g/L). Next, add the high alkaline sodium metaaluminate solution into 525 g sodium silicate (the $SiO_2$ content is 230 g/L, and the modulus is 2.9), and hold the mixture for 24h at room temperature for aging after the mixture is mixed to a homogeneous state.

Add 720 g deionized water, 222.5 g low alkaline sodium metaaluminate solution (the $Na_2O$ content is 80 g/L, and the $Al_2O_3$ content is 45 g/L) and 242 g directing agent sequentially, mix the mixture to a homogeneous state and then load it into a stainless steel reactor; hold for 24h at 100° C. for crystallization, and then filter, wash, and dry; thus, a product DLY-3 is obtained; the product properties are shown in Table 1.

Comparative Example 4

Prepare a Na—Y molecular sieve with the method disclosed in CN104773741A.

1) Load 200 g sodium silicate (the $Na_2O$ content is 6.91 wt %, and the $SiO_2$ content is 19.87 wt %) into a beaker, and place the beaker in water bath at 34° C.; add 145 g high alkaline sodium metaaluminate (the $Na_2O$ content is 21.02 wt %, and the $Al_2O_3$ content is 3.10 wt %) into the beaker quickly while stirring, and then stir for 1 h in sealed state; next, treat the mixture by aging for 16h; thus, a directing agent is obtained, and the mole ratio of material input is $16Na_2O:Al_2O_3:15\ SiO_2:325H_2O$;

2) Load 450 g sodium silicate into a beaker, and place the beaker in water bath at 50° C.; then, add 100.02 g directing agent, 149.30 g high alkaline sodium metaaluminate, and 170 g water sequentially while stirring; keep stirring for 5h, and then add 281.74 g aluminum sulfate (the $Al_2O_3$ content is 7.09 wt %) slowly, and mix and stir for 1h; thus, a gel mixture is obtained, and the mole ratio of material input is $2.5Na_2O:Al_2O_3:6.6SiO_2:207H_2O$;

3) Load the gel mixture into a reactor, and hold for 40h at 100° C. for crystallization; then, filter, wash, and dry; thus, a Na—Y molecular sieve DLY-4 is obtained; the product properties are shown in Table 1.

Example 5

First, carry out ammonium exchange for the large-grain Na—Y molecular sieve LY-1. Prepare 10 L 0.5 mol/L ammonium nitrate solution. Weigh 2,000 g small-grain Na—Y molecular sieve, dissolve it in 10 L ammonium nitrate solution prepared above, and stir for 1 h at 300 rpm stirring rate at 90° C.; then, filter the molecular sieve, and take samples to analyze the $Na_2O$ content; repeat above operations, till the $Na_2O$ content in the molecular sieve reaches 3 wt %; thus, a dried sample LYN-1 is obtained.

Weight 200 g molecular sieve LYN-1 and load it into a tubular hydrothermal treatment furnace, heat up to 530° C. by programmed heating, and treat for 1 h at 0.15 MPa gage pressure; after the hydrothermal treatment, dissolve the molecular sieve in 1 L deionized water, and heat up quickly to 80° C. while stirring at 300 rpm stirring rate. Add $(NH_4)_2SiF_6$ solution into the slurry of the molecular sieve at a constant adding rate within 2h, till 28.6.6 g $(NH_4)_2SiF_6$ is added; next, stir for 2h at a constant stirring rate at constant temperature, and the filter and dry; thus, a H—Y molecular sieve product LYNS-1 is obtained. The properties of the product are shown in Table 2.

Example 6

First, carry out ammonium exchange for the large-grain Na—Y molecular sieve LY-2. Prepare 10 L 0.5 mol/L ammonium nitrate solution. Weigh 2,000 g small-grain Na—Y molecular sieve, dissolve it in 10 L ammonium nitrate solution prepared above, and stir for 1 h at 300 rpm stirring rate at 90° C.; then, filter the molecular sieve, and take samples to analyze the $Na_2O$ content; repeat above operations, till the $Na_2O$ content in the molecular sieve reaches 2.5 wt %; thus, a dried sample LYN-2 is obtained.

Weight 200 g molecular sieve LYN-2 and load it into a tubular hydrothermal treatment furnace, heat up to 500° C. by programmed heating, and treat for 2h at 0.2 MPa gage pressure; after the hydrothermal treatment, dissolve the molecular sieve in 1 L deionized water, and heat up quickly to 75° C. while stirring at 300 rpm stirring rate. Add $(NH_4)_2SiF_6$ solution into the slurry of the molecular sieve at a constant adding rate within 2h, till 24.6.6 g $(NH_4)_2SiF_6$ is added; next, stir for 2h at a constant stirring rate at constant temperature, and the filter and dry; thus, a H—Y molecular sieve product LYNS-2 is obtained. The properties of the product are shown in Table 2.

Example 7

First, carry out ammonium exchange for the large-grain Na—Y molecular sieve LY-3. Prepare 10 L 0.5 mol/L ammonium nitrate solution. Weigh 2,000 g small-grain Na—Y molecular sieve, dissolve it in 10 L ammonium nitrate solution prepared above, and stir for 1 h at 300 rpm stirring rate at 90° C.; then, filter the molecular sieve, and take samples to analyze the $Na_2O$ content; repeat above operations, till the $Na_2O$ content in the molecular sieve reaches 2.5 wt %; thus, a dried sample LYN-3 is obtained.

Weight 200 g molecular sieve LYN-3 and load it into a tubular hydrothermal treatment furnace, heat up to 590° C. by programmed heating, and treat for 2h at 0.3 MPa gage pressure; after the hydrothermal treatment, dissolve the molecular sieve in 1 L deionized water, and heat up quickly to 100° C. while stirring at 300 rpm stirring rate. Add $(NH_4)_2SiF_6$ solution into the slurry of the molecular sieve at a constant adding rate within 2h, till 38.6.6 g $(NH_4)_2SiF_6$ is added; next, stir for 2h at a constant stirring rate at constant temperature, filter and dry; thus, a H—Y molecular sieve product LYNS-3 is obtained. The properties of the product are shown in Table 2.

Example 8

First, carry out ammonium exchange for the large-grain Na—Y molecular sieve LY-4. Prepare 10 L 0.5 mol/L ammonium nitrate solution. Weigh 2,000 g small-grain Na—Y molecular sieve, dissolve it in 10 L ammonium nitrate solution prepared above, and stir for 1 h at 300 rpm stirring rate at 90° C.; then, filter the molecular sieve, and take samples to analyze the $Na_2O$ content; repeat above operations, till the $Na_2O$ content in the molecular sieve reaches 2.5 wt %; thus, a dried sample LYN-4 is obtained.

Weight 200 g molecular sieve LYN-4 and load it into a tubular hydrothermal treatment furnace, heat up to 650° C. by programmed heating, and treat for 1 h at 0.4 MPa gage pressure; after the hydrothermal treatment, dissolve the molecular sieve in 1 L deionized water, and heat up quickly to 120° C. while stirring at 300 rpm stirring rate. Add $(NH_4)_2SiF_6$ solution into the slurry of the molecular sieve at a constant adding rate within 2h, till 67.6 g $(NH_4)_2SiF_6$ is added; next, stir for 2h at a constant stirring rate at constant temperature, and the filter and dry; thus, a H—Y molecular sieve product LYNS-4 is obtained. The properties of the product are shown in Table 2.

Example 9

Load 111.1 g molecular sieve LYNS-1 (90 wt % on dry basis), 100 g macropore alumina (1.0 mL/g pore volume, 400 m²/g specific surface area, and 70 wt % on dry basis), 100 g binder (micropore alumina, with 0.40-0.56 mL/g pore volume, 30 wt % on dry basis, and mole ratio of nitric acid to micropore alumina equal to 0.4) into a grinder for mixed grinding, add water and grind to a paste state, and extrude into strips; dry the extruded strips for 4h at 110° C., and then calcinating for 4h at 550° C.; thus, a support FHS-1 is obtained.

Impregnate the support with an impregnation liquid that contains wolframium and nickel for 2h; then, dry for 4h at 120° C., and heat up to 500° C. by programmed heating and then calcinating for 4h; thus, a catalyst CAT-1 is obtained. The compositions of the support and catalyst are shown in Table 3.

Examples 10-12

Use the method described in the example 9, but replace "LYNS-1" with "LYNS-2", "LYNS-3", and "LYNS-4" respectively; thus, supports FHS-2, FHS-3 and FHS-4 and catalysts CAT-2, CAT-3 and CAT-4 are obtained respectively. The compositions are shown in Table 3.

Comparative Examples 5-8

Use the method described in the example 5, but replace "LY-1" with "DLY-1", "DLY-2", "DLY-3" and "DLY-4" respectively; thus, H—Y molecular sieves DLYNS-1, DLYNS-2, DLYNS-3 and DLYNS-4 are obtained respectively. The product properties are shown in Table 2.

Use the method described in the example 9, but replace "LYNS-1" with "DLYNS-1", "DLYNS-2", "DLYNS-3" and "DLYNS-4" respectively; thus, supports DFHS-1, DFHS-2, DFHS-3 and DFHS-4 and catalysts DCAT-1, DCAT-2, DCAT-3 and DCAT-4 are obtained respectively. The compositions of the supports and catalysts are shown in Table 3.

Example 13

Treat poor-quality input material HLCO and high dry-point VGO with CAT-1. The properties of the raw oils are listed in Table 4, and the comparative assessment results of the hydrocracking catalysts are listed in Table 5 and Table 6.

Examples 14-16

Use the method described in the example 13, but replace "CAT-1" with "CAT-2", "CAT-3" and "CAT-4" respectively. The comparative assessment results of the hydrocracking catalysts are listed in Table 5 and Table 6.

Comparative Examples 9-12

Use the method described in the example 13, but replace "CAT-1" with "DCAT-1", "DCAT-2", "DCAT-3" and "DCAT-4" respectively. The comparative assessment of results the hydrocracking catalysts are listed in Table 5 and Table 6.

TABLE 1

|  | Example No. | | | |
| --- | --- | --- | --- | --- |
|  | LY-1 | LY-2 | LY-3 | LY-4 |
| Specific surface area, m²/g | 897 | 906 | 956 | 918 |
| Pore volume, cm³/g | 0.35 | 0.34 | 0.37 | 0.33 |
| External specific surface area, m²/g | 80 | 75 | 82 | 79 |
| Crystal cell constant, nm | 2.465 | 2.462 | 2.463 | 2.465 |
| Relative crystallinity, % | 118 | 126 | 128 | 116 |
| Average grain size, μm | 3.0 | 3.5 | 2.5 | 4.5 |
| $SiO_2/Al_2O_3$ mole ratio | 5.68 | 5.84 | 5.32 | 5.10 |
| Sum of pore volumes of pores in 1 nm-10 nm diameter to total pore volume, % | 78 | 83 | 87 | 82 |
| Relative crystallinity after calcination*, % | 95 | 98 | 92 | 93 |
| Relative crystallinity after hydrothermal treatment*, % | 108 | 112 | 115 | 104 |

|  | Comparative Example No. | | | |
| --- | --- | --- | --- | --- |
|  | DLY-1 | DLY-2 | DLY-3 | DLY-4 |
| Specific surface area, m²/g | 840 | 820 | 738 | 719 |
| Pore volume, cm³/g | 0.32 | 0.32 | 0.30 | 0.31 |
| External specific surface area, m²/g | 150 | 132 | 121 | 110 |
| Crystal cell constant, nm | 2.468 | 2.468 | 2.472 | 2.743 |
| Relative crystallinity, % | 96 | 146.7 | 92 | 102 |
| Average grain size, μm | 0.95 | 1.80 | 1.10 | 3.0 |
| $SiO_2/Al_2O_3$ mole ratio | 4.21 | 4.35 | 5.10 | 5.17 |
| Sum of pore volumes of pores in 1 nm-10 nm diameter to total pore volume, % | 51 | 56 | 43 | 29 |
| Relative crystallinity after calcination*, % | 69 | 81 | 44 | 79 |
| Relative crystallinity after hydrothermal treatment*, % | 70 | 70 | 76 | 58 |

Note:
*The conditions of calcination are: calcination for 3 h at 600° C. in air;
*The conditions of hydrothermal treatment are: treat for 1 h at 650° C. in water vapor.

TABLE 2

|  | Example No. | | | |
| --- | --- | --- | --- | --- |
|  | LYNS-1 | LYNS-2 | LYNS-3 | LYNS-4 |
| Specific surface area, m²/g | 920 | 899 | 965 | 947 |
| Pore volume, cm³/g | 0.44 | 0.45 | 0.46 | 0.47 |
| Crystal cell constant, nm | 2.440 | 2.442 | 2.433 | 2.428 |
| Relative crystallinity, % | 133 | 130 | 136 | 143 |
| Average grain size, μm | 3.0 | 3.0 | 3.0 | 3.0 |
| $SiO_2/Al_2O_3$ mole ratio | 33.5 | 28.4 | 69.8 | 105.6 |
| Sum of pore volumes of pores in 3 nm-7 nm diameter to total pore volume, % | 78 | 75 | 83 | 91 |
| Percentage of amount of non-skeleton aluminum to total aluminum content, % | 0.3 | 0.1 | 0.2 | 0.1 |
| Total acid amount measured by NIS, mmol/g | 0.67 | 0.75 | 0.42 | 0.28 |
| $Na_2O$, wt % | 0.12 | 0.10 | 0.10 | 0.09 |

|  | Comparative Example No. | | | |
| --- | --- | --- | --- | --- |
|  | DYNS-1 | DYNS-2 | DYNS-3 | DYNS-4 |
| Specific surface area, m²/g | 611 | 650 | 569 | 585 |
| Pore volume, cm³/g | 0.36 | 0.35 | 0.37 | 0.36 |
| Crystal cell constant, nm | 2.443 | 2.439 | 2.429 | 2.431 |
| Relative crystallinity, % | 91 | 81 | 79 | 81 |
| Average grain size, μm | 0.95 | 0.95 | 0.95 | 0.95 |
| $SiO_2/Al_2O_3$ mole ratio | 9.8 | 15.3 | 16.9 | 23.5 |
| Sum of pore volumes of pores in 3 nm-7 nm diameter to total pore volume, % | 29 | 32 | 36 | 33 |
| Percentage of amount of non-skeleton aluminum to total aluminum content, % | 1.8 | 1.5 | 1.8 | 2.1 |
| Total acid amount measured by NIS, mmol/g | 1.02 | 0.87 | 0.29 | 0.38 |
| $Na_2O$, wt % | 0.16 | 0.18 | 0.16 | 0.18 |

TABLE 3

| | Examples | | | |
|---|---|---|---|---|
| | Support | | | |
| | FHS-1 | FHS-2 | FHS-3 | FHS-4 |
| Modified Y molecular sieve, wt % | 25.0 | 25.0 | 25.0 | 25.0 |
| Macro-pore alumina, wt % | 40.0 | 40.0 | 40.0 | 40.0 |
| Binder, wt % | 35 | 35 | 35 | 35 |
| | Catalyst | | | |
| | CAT-1 | CAT-2 | CAT-3 | CAT-4 |
| $WO_3$, wt % | 22.50 | 22.51 | 22.48 | 22.49 |
| NiO, wt % | 6.02 | 5.97 | 6.03 | 6.02 |
| | Comparative Examples | | | |
| | Support | | | |
| | DFHS-1 | DFHS-2 | DFHS-3 | DFHS-4 |
| Modified Y molecular sieve, wt % | 25.0 | 25.0 | 25.0 | 25.0 |
| Macro-pore alumina, wt % | 40.0 | 40.0 | 40.0 | 40.0 |
| Binder, wt % | 35 | 35 | 35 | 35 |
| | Catalyst | | | |
| | DCAT-1 | DCAT-2 | DCAT-3 | DCAT-4 |
| $WO_3$, wt % | 22.48 | 22.49 | 22.51 | 22.36 |
| NiO, wt % | 6.01 | 6.02 | 5.99 | 5.87 |

TABLE 4

| | Raw oil | |
|---|---|---|
| | HLCO | VGO |
| Density (@ 20° C.), g/cm³ | 0.9440 | 0.9096 |
| Distillation range, ° C. | | |
| IBP/10% | 136/227 | 305/361 |
| 30%/50% | 252/275 | 394/417 |
| 70%/90% | 303/343 | 443/481 |
| 95%/EBP | 357/371 | 509/533 |
| Pour point, ° C. | −24 | 33 |
| Cetane number | 15 | |
| Cetane index (ASTMD 4737-96a) | 23.8 | |
| S, wt % | 0.81 | 1.98 |
| N, μg/g | 914 | 1228 |
| C, wt % | 89.70 | 85.28 |
| H, wt % | 9.40 | 12.46 |
| BMCI value | | 45.0 |

TABLE 5

| | Raw oil | | | |
|---|---|---|---|---|
| | HLCO | HLCO | HLCO | HLCO |
| | Catalyst | | | |
| | CAT-1 | DCAT-1 | DCAT-2 | DCAT-3 |
| Total reaction pressure, MPa | 14.7 | 14.7 | 14.7 | 14.7 |
| Total LHSV, h⁻¹ | 1.2 | 1.2 | 1.2 | 1.2 |
| Volume ratio of hydrogen/oil | 1200:1 | 1200:1 | 1200:1 | 1200:1 |
| Reaction temperature, ° C. | 385 | 390 | 401 | 393 |

TABLE 5-continued

| | Raw oil | | | |
|---|---|---|---|---|
| | HLCO | HLCO | HLCO | HLCO |
| | Catalyst | | | |
| | CAT-1 | DCAT-1 | DCAT-2 | DCAT-3 |
| Product Distribution and Major Product Properties | | | | |
| Fraction <65° C. | | | | |
| Yield, wt % | 5.97 | 6.55 | 7.65 | 6.89 |
| Octane number (RON) | 85.5 | 85.4 | 82.11 | 84.61 |
| Fraction within 65° C.-165° C. range | | | | |
| Yield, wt % | 50.35 | 44.70 | 46.69 | 45.11 |
| Aromatic potential, wt % | 75.5 | 72.1 | 68.5 | 70.3 |
| Fraction >165° C. | | | | |
| Yield, wt % | 35.09 | 37.78 | 35.50 | 36.08 |
| Cetane index (ASTMD 4737-96a) | 41.8 | 38.3 | 37.5 | 39.1 |

TABLE 6

| | Raw oil | | | |
|---|---|---|---|---|
| | VGO | VGO | VGO | VGO |
| | Catalyst in the example | | | |
| | CAT-1 | CAT-2 | CAT-3 | CAT-4 |
| LHSV, h⁻¹ | 1.0 | 1.0 | 1.0 | 1.0 |
| Volume ratio of hydrogen/oil | 1200:1 | 1200:1 | 1200:1 | 1200:1 |
| Total reaction pressure, MPa | 14.7 | 14.7 | 14.7 | 14.7 |
| Reaction temperature, ° C. | 390 | 392 | 391 | 393 |
| Product Yield and Properties | | | | |
| Heavy naphtha | | | | |
| Yield, % | 8.8 | 9.2 | 9.1 | 9.6 |
| Aromatic potential, wt % | 62.7 | 61.5 | 62.9 | 61.9 |
| Jet fuel | | | | |
| Yield, % | 23.1 | 23.8 | 23.8 | 24.3 |
| Smoke point, mm | 23 | 24 | 25 | 25 |
| Aromatics, v % | 10.0 | 9.8 | 8.7 | 8.6 |
| Diesel oil | | | | |
| Yield, % | 35.5 | 34.6 | 34.1 | 34..0 |
| Cetane number | 62.0 | 63.0 | 65.0 | 65.0 |
| Tailings | | | | |
| Yield, % | 28.9 | 28.1 | 28.0 | 28.5 |
| BMCI value | 9.0 | 8.5 | 7.3 | 7.0 |
| Chemical hydrogen consumption, wt % | 2.18 | 2.19 | 2.20 | 2.20 |
| Liquid yield, % | 98.4 | 98.3 | 98.3 | 98.2 |
| | Catalyst in comparative example | | | |
| | DCAT-1 | DCAT-2 | DCAT-3 | DCAT-4 |
| LHSV, h⁻¹ | 1.0 | 1.0 | 1.0 | 1.0 |
| Volume ratio of hydrogen/oil | 1200:1 | 1200:1 | 1200:1 | 1200:1 |
| Total reaction pressure, MPa | 14.7 | 14.7 | 14.7 | 14.7 |
| Reaction temperature, ° C. | 396 | 400 | 398 | 407 |

TABLE 6-continued

Product Yield and Properties

| | | | | |
|---|---|---|---|---|
| Heavy naphtha | | | | |
| Yield, % | 9.9 | 10.6 | 10.5 | 11.2 |
| Aromatic potential, wt % | 61.6 | 59.8 | 59.9 | 57.6 |
| Jet fuel | | | | |
| Yield, % | 22.6 | 23.2 | 24.0 | 25.6 |
| Smoke point, mm | 22 | 23 | 21 | 22 |
| Aromatics, v % | 12.5 | 11.8 | 15.6 | 14.7 |
| Diesel oil | | | | |
| Yield, % | 33.2 | 31.5 | 32.3 | 33.2 |
| Cetane number | 60.1 | 61.2 | 59.6 | 57.3 |
| Tailings | | | | |
| Yield, % | 28.0 | 26.0 | 25.6 | 26.8 |
| BMCI value | 10.8 | 10.3 | 11.3 | 11.0 |
| Chemical hydrogen consumption, wt % | 2.24 | 2.32 | 2.30 | 2.36 |
| Liquid yield, % | 97.6 | 97.1 | 96.8 | 96.8 |

It can be seen from the examples, comparative examples, and data in Tables 5-6: the performance of the catalysts prepared from the large-grain Na—Y molecular sieve provided in the present invention in hydrocracking reactions is superior to that of the catalysts prepared from the comparative molecular sieves.

What is claimed is:

1. A hydrocracking catalyst, wherein the support in the catalyst contains an H—Y molecular sieve, wherein the crystal cell parameter of the H—Y molecular sieve is 2.425-2.450 nm; the mole ratio of $SiO_2/Al_2O_3$ in the H—Y molecular sieve is 10-120:1; the sum of pore volumes of pores in 2-7 nm diameter in the H—Y molecular sieve is 60-95% of the total pore volume; the specific surface area of the H—Y molecular sieve is 750-980 $m^2/g$; and, the total acid amount measured by near infrared spectroscopy in the H—Y molecular sieve is 0.1-1.0 mmol/g.

2. The hydrocracking catalyst according to claim 1, wherein the crystal cell parameter of the H—Y molecular sieve is 2.436-2.450 nm; the mole ratio of $SiO_2/Al_2O_3$ in the H—Y molecular sieve is 10-50:1; the sum of pore volumes of pores in 2-6 nm diameter in the H—Y molecular sieve is 60-90% of the total pore volume; the specific surface area of the H—Y molecular sieve is 750-950 $m^2/g$; and, the total acid amount measured by near infrared spectroscopy in the H—Y molecular sieve is 0.5-1.0 mmol/g.

3. The hydrocracking catalyst according to claim 1, wherein the crystal cell parameter of the H—Y molecular sieve is 2.425-2.435 nm; the mole ratio of $SiO_2/Al_2O_3$ in the H—Y molecular sieve is 60-120:1; the sum of pore volumes of pores in 3-7 nm diameter in the H—Y molecular sieve is 70-95% of the total pore volume; the specific surface area of the H—Y molecular sieve is 800-980 $m^2/g$; and, the total acid amount measured by near infrared spectroscopy in the H—Y molecular sieve is 0.1-0.5 mmol/g.

4. The hydrocracking catalyst according to claim 1, wherein the content of the H—Y molecular sieve in the support is 15-90 wt %.

5. The hydrocracking catalyst according to claim 1, wherein the specific surface area of the hydrocracking catalyst is 200-400 $m^2/g$, and the pore volume of the hydrocracking catalyst is 0.2-0.5 ml/g.

6. The hydrocracking catalyst according to claim 1, wherein further comprising a hydrogenation active component, the hydrogenation active component is an metal element in VIB Family and an metal element in VIII Family.

7. The hydrocracking catalyst according to claim 6, wherein based on the total weight of the hydrocracking catalyst and calculated in metal oxide, the content of the metal element in VIB Family is 10-40 wt %, and the content of the metal element in VIII Family is 3-15 wt %; the content of the support is 45-87 wt %.

* * * * *